(12) United States Patent
Hall et al.

(10) Patent No.: US 6,542,766 B2
(45) Date of Patent: Apr. 1, 2003

(54) MEDICAL DEVICES ADAPTED FOR MAGNETIC NAVIGATION WITH MAGNETIC FIELDS AND GRADIENTS

(76) Inventors: Andrew F. Hall, 4041 Forest Park Ave., St. Louis, MO (US) 63108; Roger N. Hastings, 4041 Forest Park Ave., St. Louis, MO (US) 63108; Rogers C. Ritter, 4041 Forest Park Ave., St. Louis, MO (US) 63108

( * ) Notice: Subject to any disclaimer, the term of this patent is extended or adjusted under 35 U.S.C. 154(b) by 0 days.

(21) Appl. No.: 09/909,188

(22) Filed: Jul. 19, 2001

(65) Prior Publication Data

US 2001/0047129 A1 Nov. 29, 2001

Related U.S. Application Data

(62) Division of application No. 09/311,686, filed on May 13, 1999, now Pat. No. 6,292,678.

(51) Int. Cl.[7] .................. A61B 5/042; A61B 18/14; A61H 1/05
(52) U.S. Cl. ............ 600/374; 600/585; 604/95.05; 604/510; 604/528; 606/21; 606/27; 606/41; 607/119; 607/122
(58) Field of Search .................. 600/12, 373, 374, 600/585; 606/41, 21, 27; 604/95.05, 510, 528; 607/119, 122

(56) References Cited

U.S. PATENT DOCUMENTS

| | | | | |
|---|---|---|---|---|
| 3,794,041 A | * | 2/1974 | Frei et al. | 600/12 |
| 5,776,080 A | * | 7/1998 | Thome et al. | 600/585 |
| 5,911,720 A | * | 6/1999 | Bourne et al. | 600/374 |
| 6,126,647 A | * | 10/2000 | Posey et al. | 600/12 |
| 6,129,685 A | * | 10/2000 | Howard, III | 600/373 |
| 6,272,370 B1 | * | 8/2001 | Gillies et al. | 324/309 |

* cited by examiner

Primary Examiner—Lee Cohen

(57) ABSTRACT

A method of applying an elongate magnetic element to the surface of an internal body structure includes applying a magnetic field to the elongate magnetic element to orient the elongate magnetic element in a selected orientation; and applying a magnetic gradient to the elongate magnetic element to draw the elongate magnetic element against the surface of the body structure.

11 Claims, 7 Drawing Sheets

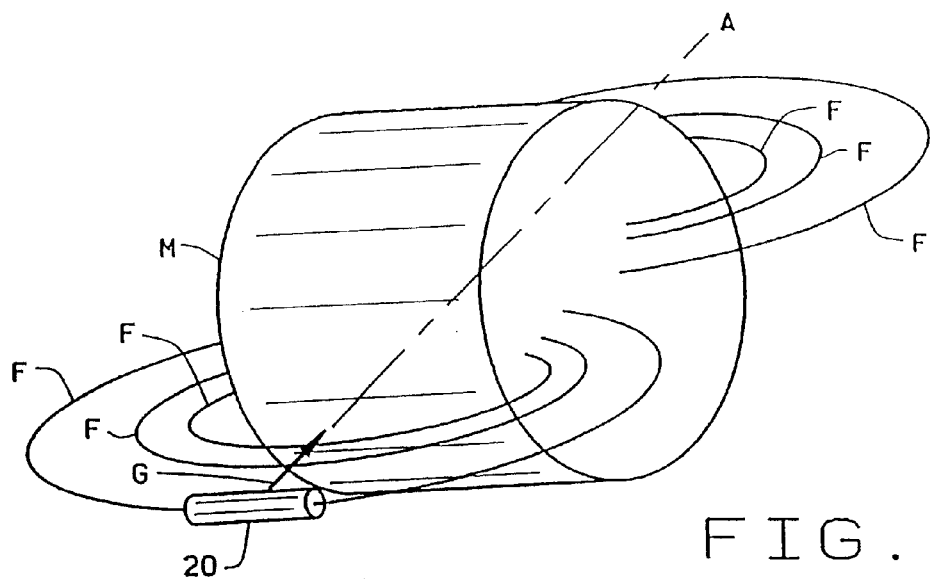
FIG. 1C
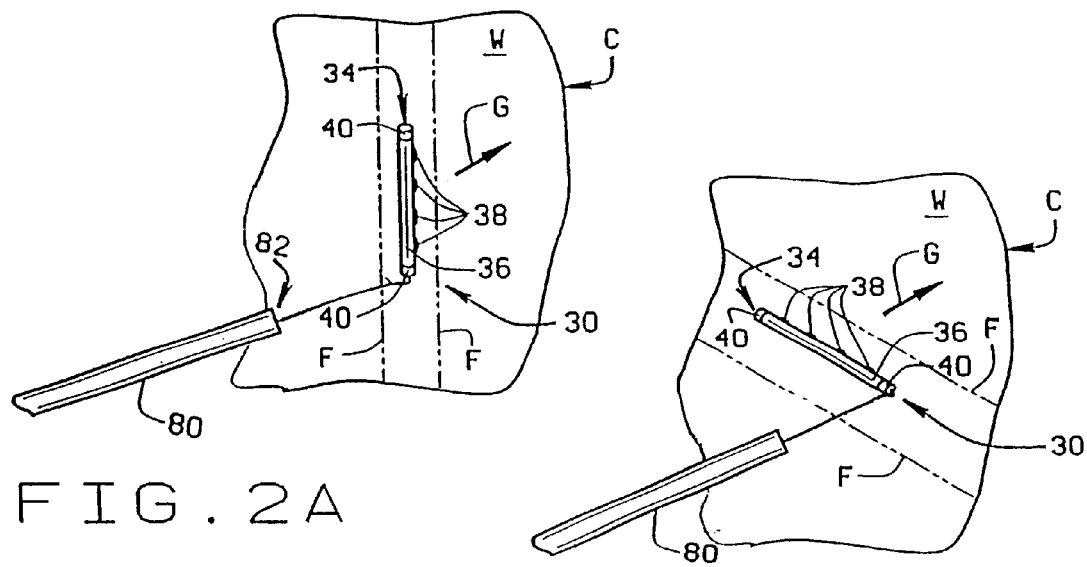
FIG. 2A
FIG. 2B
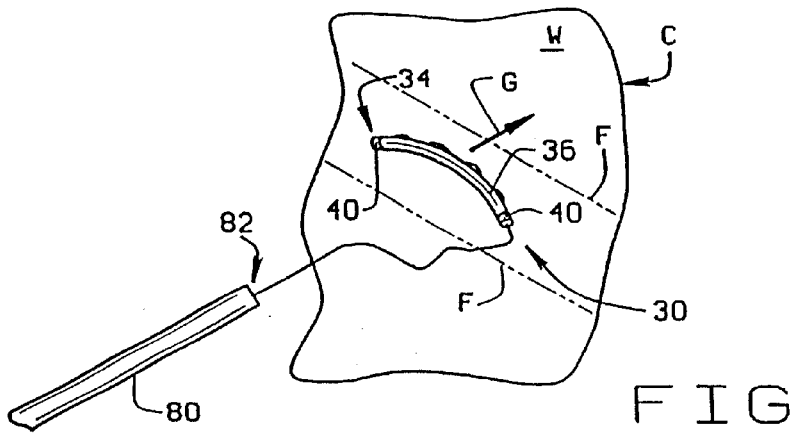
FIG. 2C

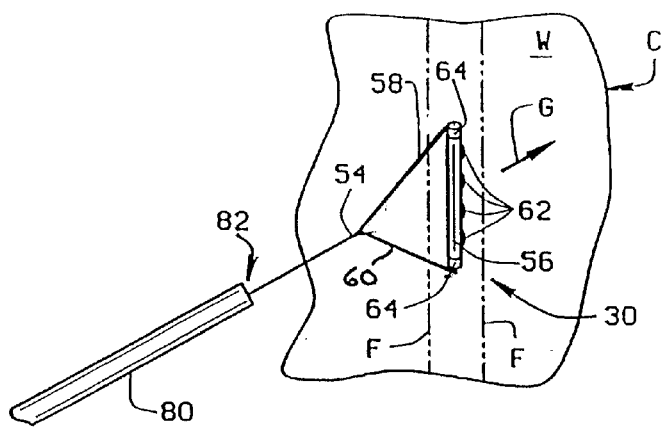
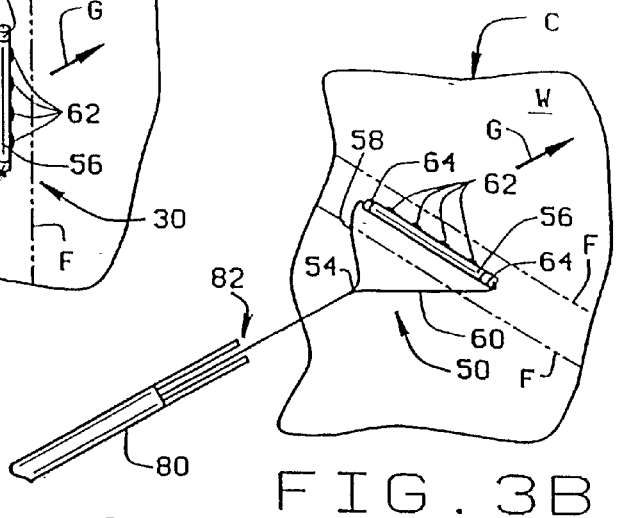
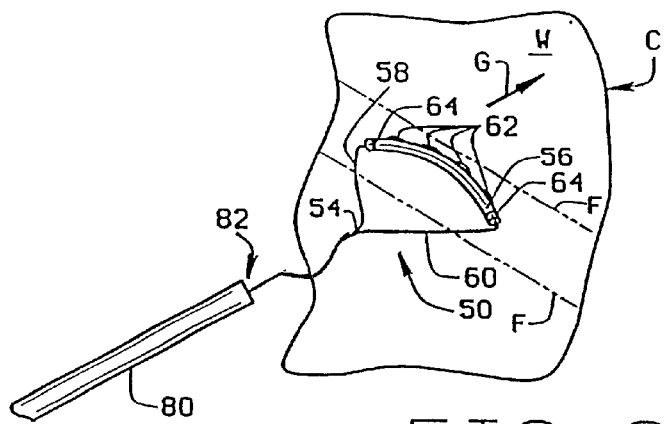
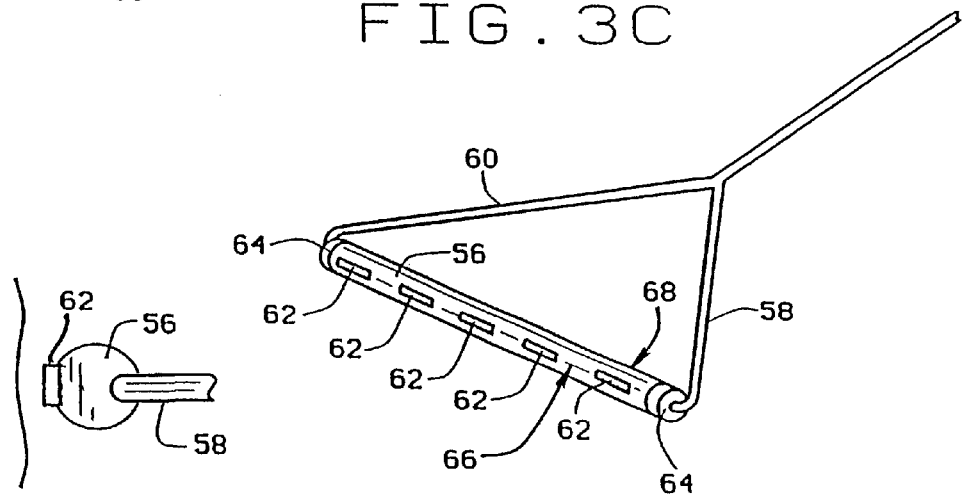
FIG. 3A
FIG. 3B
FIG. 3C
FIG. 5
FIG. 4

MEDICAL DEVICES ADAPTED FOR MAGNETIC NAVIGATION WITH MAGNETIC FIELDS AND GRADIENTS

CROSS-REFERENCE TO RELATED APPLICATIONS

This application is a divisional of U.S. patent application Ser. No. 09/311,686 filed on May 13, 1999, now U.S. Pat. No. 6,292,678. The disclosure of which is incorporated herein by reference.

FIELD OF THE INVENTION

This invention relates to a method of magnetically navigating medical devices in the body with a combination of a magnetic field and a magnetic gradient, and to medical devices adapted therefor.

BACKGROUND OF THE INVENTION

Magnets have long been used to navigate objects in the body. The earliest use of magnets was for removing magnetic materials, such as steel shrapnel, from a patient's body. Subsequently, magnets were used to move medical devices in the body. More specifically, magnets have also been used to create a magnetic field in the body for orienting magnetic medical devices, or to create a front field magnetic gradient (i.e., a gradient substantially aligned with the magnetic field) for pulling magnetic medical devices in the body. There are a number of medical applications in which it is desirable to both orient a medical device and apply it against an internal body structure in the selected orientation, for example in cardiac mapping, cardiac pacing, or cardiac ablation procedures. This ability would also be useful in the targeted delivery of therapeutic agents, for example delivery of growth agents for percutaneous myocardio revascularization. While magnetic fields have proven effective for orienting medical devices in the body, and to a lesser extent end field magnetic gradients have proven effective for moving medical devices in the body, its has not been possible to orient a medical device and apply it against an internal body structure in the selected orientation.

The ability to orient and apply a medical device against an internal body structure would have a wide range of medical applications, and particularly in cardiac electrophysiology. There are several types of abnormally rapid heart rhythms, or tachyarrhythmias. Over the past decade, reliable cures for some of these tachyarrhythmias have been developed using catheter-based radio frequency (RF) energy to ablate the piece of cardiac tissue responsible for the arrhythmia. These conditions include Wolfe Parkinson White syndrome and Atrio-Ventricular Nodal Reentrant Tachycardias, where procedural success rates are as high as 99–100%. The catheters used for RF ablation have one or more electrodes at the distal end and typically contain a means for manual mechanical navigation with a heart chamber. The physician uses controls at the proximal end of the catheter to navigate the distal tip to the desired location and to attempt to hold it in constant contact with the heart wall during the application of RF energy.

More recently, much attention has been paid to another cardiac tachyarrhythmia, atrial fibrillation (AF). AF is characterized by a rapid, disorganized beating of both atria. AF affects over 2 million people in the U.S., mostly those over 60. While AF is not acutely life threatening, it can have debilitating symptoms and raises the risk of stoke (via embolized thrombus formed in the stagnant atria) by a factor of 5. The only curative procedure to date for AF is the surgical Maze procedure, developed in the mid-1980's at Washington University in St. Louis. As described in Cox et al., J Thorac Cardiovasc Surg 1995,110, 473–495, (incorporated herein by reference), several transmural incisions are made in both atria (in a particular anatomic pattern), interrupting the fibrillatory "circuits" in the tissue while allowing conduction to proceed in a circuitous path throughout the atria.

Substantial work has been done to attempt to mimic the Maze procedure with a less invasive, percutaneous approach. This work has resulted in the development of a number of "linear lesion catheters." These devices are designed to create transmural linear lesions which mimic the surgical incisions of the Maze procedure. While most use an array of RF electrodes (e.g. Avitall, U.S. Pat. No. 5,730,127; Li et al., U.S. Pat. No. 5,879,295; Schaer, U.S. Pat. No. 5,863,291; Chen et al., U.S. Pat. No. 5,782,828; and Pomeranz et al, U.S. Pat. No. 5,800,482, each of which is incorporated herein by reference) other tissue ablation technologies have also been incorporated into these catheters as well, such as cryogenic ablation (e.g., Avitall, U.S. Pat. No. 5,733,280, incorporated herein by reference), and ultrasound (e.g., Crowley, U.S. Pat. No. 5,630,837, incorporated herein by reference). The "catheter Maze" procedure consists of placing a series of interconnected linear lesions in both atria. For this procedure the catheter must be navigated to, and positioned at, several sites in both atria. Clearly, there is an additional constraint on navigating linear lesion catheters that is not imposed on point ablation catheters: orientation. Not only must the catheter be navigated to the proper location and held there, it must be positioned in the proper orientation.

Prior to this invention, linear lesion catheters have been navigated, positioned and held in place manually via mechanical controls at the proximal end of the catheter. The linear lesion catheters designed to date share one or more of the following problems: Most of these catheters are optimized for some locations and orientations, and are suboptimal for other orientations. The ability to navigate and position the catheter using mechanical controls is dependent on the tortuosity of the catheter's path to the chamber. The more tortuous the path, less navigational and positional ability remains once the catheter reaches the chamber. The proximal end of the catheter is stationary, while the distal segment is moving with heart chamber, making it difficult to assure good contact of all electrodes, or other lesion making surfaces, throughout the cardiac cycle. For example, if ablation electrodes are not in intimate contact with the walls of the heart, the electrodes can overheat the blood and coagulum can form on the catheter reducing its effectiveness. These limitations have proven particularly problematic when attempting to create lesions in the left atrium.

Also, since the heart wall is moving, the force supplied by traditional catheters to the heart wall varies during the cardiac cycle and the physician cannot quantitatively sense how much force is being exerted against the tissues. As a consequence the mapping and ablating process is not readily reproducible, even for endocardial sites which may be easy to navigate to.

SUMMARY OF THE INVENTION

The present invention relates to a method of navigating medical devices in the body which employs both a magnetic field to selectively orient the medical device, and a magnetic gradient to pull the medical device against a selected body structure. Generally the method comprises the steps of applying a magnetic field to the elongate magnetic element to orient the elongate magnetic element in a selected orientation; and applying a magnetic gradient to the elongate magnetic element to draw the elongate magnetic element against the surface of the body structure. The magnetic gradient is preferably oblique to the magnetic field direction, so that the pulling force is at an oblique angle to the aligning force, and more preferably the gradient is perpendicular to the field direction. Thus, the elongate magnetic element is held against the body structure substantially along its length. This can be conveniently done with one or more permanent magnets, using, for example the side field of a single permanent magnet or using the field in the gap of a gapped toroid magnet, but it could also be done with electromagnets, or superconducting electromagnets.

This present invention also relates to a magnetic medical device adapted to be applied to the internal structures of the body. Generally, the medical device includes an elongate magnetic element comprising one or more magnetically responsive bodies. The magnetically responsive bodies can comprise cylinders or coils of a permeable magnetic material or a permanent magnetic material. The magnets are preferably axially polarized so that the elongate magnetic element aligns with an applied magnetic field. The direction of the polarity of the magnet bodies with respect to the longitudinal axis of the elongate magnetic element can vary, to cause the elongate element to bend to facilitate the elongate medical device conforming to the internal body structure to which it is applied. The magnetically responsive bodies could also be spherical magnets, pivotally mounted in the elongate magnetic element so that they can align with the applied magnetic field, still apply an aligning torque to the elongate magnetic element.

The elongate magnetic element can include electrodes for mapping, electrodes for pacing, or electrodescontacts or other elements for tissue ablation. The elongate magnetic element could alternatively or additionally include injectors or simply openings for the delivery of therapeutic or other agents from the medical device, for example growth factors for percutaneous myocardial revasculariation, or simple saline for cooling the electrodes/contacts used in ablation.

The method of the present invention allows an elongate medical device to be precisely oriented and applied to the surface of an internal body structure. This facilitates a number of procedures, including cardiac mapping, cardiac pacing and cardiac ablation. The magnetic field and the oblique magnetic gradient can be easily and economically applied with a single permanent magnet, and thus the method can be employed with relatively inexpensive equipment, although the magnetic field and gradient may be applied with a gapped toroid magnet, or one or more electromagnets or superconducting electromagnets.

These and other features and advantages will be in part apparent, and in part pointed out hereinafter.

BRIEF DESCRIPTION OF THE DRAWINGS

FIG. 1C perspective view of the magnetic field and gradient applied to an elongate magnetic element by the magnet in a third orientation;

FIG. 2A is a perspective view of a first embodiment of a catheter, constructed according to the principles of this invention, shown as it is being captured by an applied magnetic field before being oriented and applied to the wall of a patient's heart;

FIG. 2B is a perspective view of the catheter of the first embodiment shown after it has been aligned on a selected orientation by the manipulation of the magnetic field direction.

FIG. 2C is a perspective view of the catheter of the first embodiment, shown as it is being applied to the wall of the patient's heart;

FIG. 3A is a perspective view of a second embodiment of a catheter, constructed according to the principles of this invention, shown as it is being captured by an applied magnetic field before being oriented and applied to the wall of a patient's heart;

FIG. 3B is a perspective view of the catheter of the second embodiment shown after it has been aligned in a selected orientation by the manipulation of the magnetic field direction.

FIG. 3C is a perspective view of the catheter of the second embodiment, shown as it is being applied to the wall of the patient's heart;

FIG. 4 is a perspective view of the catheter of the second embodiment;

FIG. 5 is an enlarged side elevation view of the catheter of the second embodiment shown as it is about to be applied to the wall of a patient's heart;

Corresponding reference numerals indicate corresponding parts throughout the several views of the drawings.

DETAILED DESCRIPTION OF THE INVENTION

According to the method of the present invention, a magnetic medical device can be oriented and applied to the surface of an internal body structure, such as the wall of the heart in a cardiac mapping, pacing, or ablation procedure. While the method and apparatus described herein relate to the application of medical devices to the heart, the invention is not so limited and the method and apparatus of this invention can be used to apply medical devices to other internal body structures as well. The method comprises applying a magnetic field to the elongate magnetic element to orient the elongate magnetic element in a selected orientation, and applying an approximately transverse magnetic gradient to the elongate magnetic element to draw the elongate magnetic element against the surface of the body structure. The magnetic field and the magnetic gradient are preferably applied simultaneously, using the side field of a magnet. The side field of a magnet has a magnetic gradient oblique to the magnetic field direction, and thus is useful in aligning a magnetic medical device with the magnetic field, and pulling the magnetic medical device in an oblique direction.

The magnetic field and gradient can be simultaneously applied with a single permanent magnet, a pair of permanent magnets (for example in a gapped toroid arrangement), a single electromagnetic coil (preferably a superconducting electromagnetic coil), or a pair of electromagnetic coils (preferably superconducting electromagnetic coils).

Figure 1A:
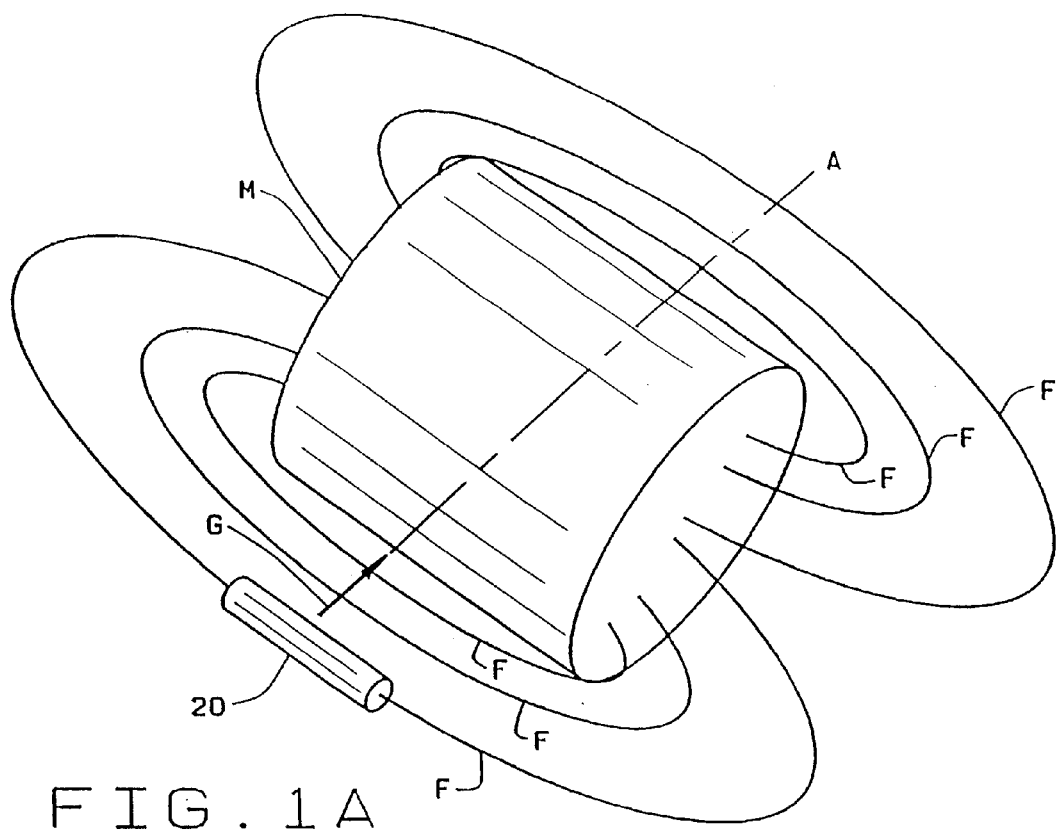
FIG. 1A is a perspective view of the magnetic field and gradient applied to an elongate magnetic element by a magnet in a first orientation.
Figure 1B:
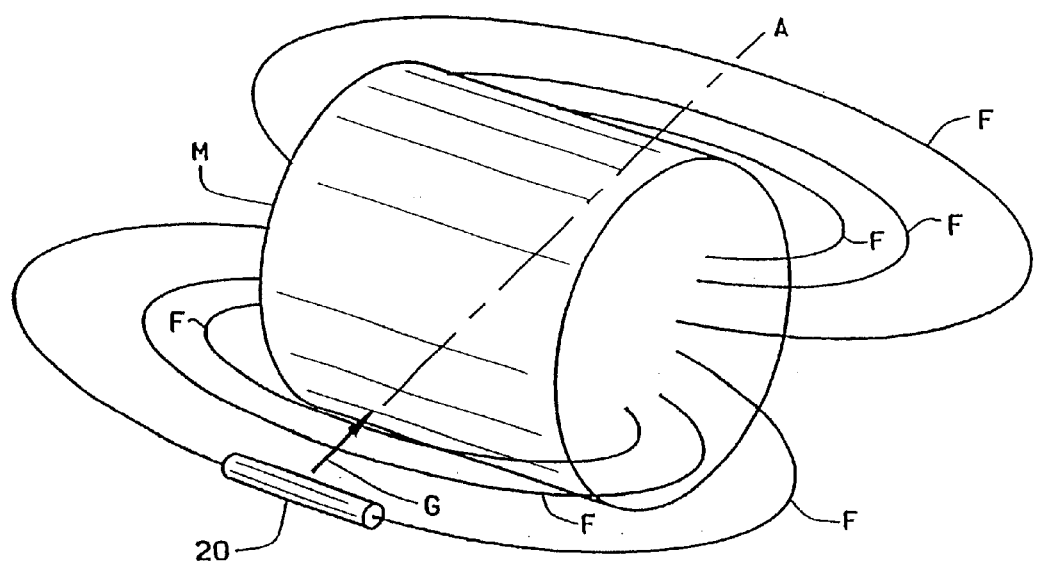
FIG. 1B is a perspective view of the magnetic field and gradient applied to an elongate magnetic element by the magnet in a second orientation.

The orientation of the elongate magnetic element can be changed by changing the direction of the applied magnetic field. This can be done by moving or changing the orientation of the source of the applied magnetic field and gradient. FIG. 1A is a perspective view showing the magnetic field lines F and the direction of the magnetic gradient G applied to an elongate magnetic element 20 by a magnet M in a first orientation. FIG. 1B shows the magnetic field lines F and the direction of the magnetic gradient G applied to the magnetic element 20 by the magnet M in a second orientation, rotated about axis A. FIG. 1C shows the magnetic field lines F and the direction of the magnetic gradient G applied to the magnetic element 20 by the magnet M in a third orientation, rotated about axis A. FIGS. 1A through 1C illustrate that by changing the direction of the magnetic field lines, by moving the magnet M, the orientation of the elongate magnetic element 20 can be changed, while the direction of the magnetic gradient remains generally perpendicular to the field lines.

As shown in FIGS. 1A through 1C, the polarity of magnet M is aligned with its axis.

The side field of the magnet M is capable of creating a magnetic field and an oblique magnetic gradient in an operating region in a patient, to control a magnetic medical device in the operating region in a patient. The medical device is localized in the operating region, for example with bi-planar fluoroscopy, ultrasonic time-of-flight, or electromagnetic means, so that the physician can monitor the location and orientation of the device in space, or relative to the tissue to be interacted with (using whatever visualization is provided as part of the magnetic navigation system). The physician can then manually orient the magnet; input desired orientation and direction of movement to a computer controller that operates an articulated arm to orient the magnet; or otherwise control the position and orientation of the source of the magnetic field and gradient.

Referring to FIGS. 2A through 2C, a magnetic medical device, such as a catheter 30, is navigated to the operating region, for example the chamber C of a heart, as described in more detail below. The catheter 30 has a proximal end and a distal end 34. An elongate magnetic element 36 is formed on the distal end 34 of the catheter 30. As shown in FIG. 2A, a magnetic field and gradient are applied to the operating region. The elongate magnetic element 36 aligns the distal end 34 of the catheter 30 with the magnetic field lines established within the operating region, and the elongate magnetic element pulls the distal end of the catheter in the direction of the magnetic gradient established in the operating region to the wall W of the chamber C of the heart. See FIG. 2A. The elongate magnetic element is then oriented by moving and or rotating the source of the magnetic field to change the local magnetic field direction. See FIG. 2B. Tension on the proximal portion of the catheter 30 restrains distal end 34 of the catheter against the force of the magnetic gradient, so that the magnetic field can be manipulated to align elongate magnet element 36, and thus the distal end of the catheter, in the desired orientation without interference from the surface of the internal structure.

As shown in FIG. 2C, once the distal end 34 of the catheter 30 is in the desired orientation, the tension on the proximal end of the catheter can be slacked to allow the distal end of the catheter to move under the force of the magnetic gradient to contact the wall W of the chamber C of the heart. The elongate magnetic element 36 preferably conforms to the shape of the wall W of the chamber C of the heart. (Although the surface of the wall W also conforms somewhat to the shape of the elongate magnetic element 36). The catheter 30 can then be used to conduct a medical procedure, for example the elongate magnetic element 36 can be provided with contacts 38, such as electrodes for electrically mapping the heart, pacing the heart, or ablating heart tissue. The elongate magnetic element 36 could alternatively be provided with some other type of contacts 38, such as cryogenic contacts for ablating the tissue with low temperature or ultrasonic transducers for ablating tissue ultrasonically. The elongate magnetic element 36 could alternatively be provided, with injectors or simply openings for delivering substances for example medications, such as growth factors for revascularization, directly to the heart tissue. Openings can also be provided to inject fluid, such as saline solution, to cool, and thereby improve the efficiency of the ablation contacts.

Markers 40 on the catheter 30, positioned, for example at the ends of the elongate magnetic element 36, help the physician visualize the catheter and thereby properly position and orient the catheter. The markers 40 could be radio-opaque where the catheter is localized with fluoroscopy; ultrasonic transducers, where the catheter is localized using ultrasonic time-of-flight; electromagnetic means, where the catheter is localized using electromagnetic field sensing; or some other type of marker for localizing the catheter.

By locating the catheter 30 with the markers 40, the force applied to the catheter can be calculated knowing the relationship (distance and angle) between the catheter and the source of the magnetic field, and thus the physician can know the force holding the catheter in contact with the wall W of the chamber of the heart. The torque on the catheter can also be calculated knowing the location and orientation of the distal segment and the angle of the applied magnetic field. The physician can manipulate the magnet to control the amount of force that the catheter 30 applies to the wall of the heart, to ensure proper contact between the contacts 38 or other devices provided on the elongate magnetic element 36 for conducting the medical procedure. Prior to this invention, achieving a specified minimum contact pressure between a catheter and a moving structure such as the heart wall, was extremely difficult.

Referring to FIGS. 3A through 3C, a magnetic medical device, such as a catheter 50, is navigated to the operating region, for example the chamber C of a heart, as described in more detail below. The catheter 50 has a proximal end and a distal end 54. An elongate magnetic element 56 is formed on the distal end 54, and secured at each end to the distal end of the catheter 50 with tethers 58 and 60. A magnet field and gradient are applied to the operating region. The elongate magnetic element 56 aligns with the magnetic field lines established within the operating region, and the elongate magnetic element is pulled in the direction of the magnetic gradient established in the operating region toward the wall W of the chamber C of the heart. See FIG. 3A. The elongate magnetic element is then oriented, by moving and or rotating the source of the magnetic field to change the local magnetic field direction. See FIG. 3B. The proximal portion of the catheter 50 holds the elongate magnetic element of the catheter against the force of the magnetic gradient, so that the magnetic field can be manipulated to align the elongate magnetic element in the desired orientation.

As shown in FIG. 3C, once the elongate magnetic element 56 is in the desired orientation, it can be released by slacking the tension on the tethers 58 and 60 or on the proximal portion of the catheter 50 so that the elongate magnetic element can move under the force of the magnetic gradient to contact the wall W of the chamber C of the heart. The catheter 50 can then be used to conduct a medical procedure, for example the elongate magnetic element 56 can be provided with contacts 62, such as electrodes for electrically mapping the heart, for pacing the heart, or for ablating the heart tissue. The catheter 50 could alternatively be provided with some other type of contacts 62 such as ultrasonic transducers for ablating tissue ultrasonically. The catheter 50 could alternatively be provided with some type of continuous linear ablation segment, such as cryogenic contacts for ablating tissue with low temperature. The catheter 50 could also be provided with injectors or openings for delivering medications, such as growth factors directly to the heart tissue. Openings can also be provided to inject fluid, such as saline solution, to cool, and thereby improve the efficiency of the ablation contacts.

Markers 64 on the catheter 50, positioned for example at the ends of the elongate magnetic element 56, help the physician visualize the catheter and thereby properly position and orient the catheter. The markers 64 could be radio-opaque where the catheter is localized with fluoroscopy; ultrasonic transducers where the catheter is localized using ultrasonic time-of-flight; electromagnetic means where the catheter is localized using electromagnetic field sensing or some other type of marker for localizing the catheter.

By locating the catheter 50 with the markers 64, the force applied to the catheter can be calculated knowing the relationship (distance and angle) between the catheter and the source of the magnetic field, and thus the physician can know the force holding the catheter in contact with the wall of the chamber of the heart. The torque on the catheter tip can also be calculated knowing the orientation and location of the distal segment and the magnitude and orientation of the applied magnetic field. The physician can manipulate the magnet to control the amount of force the catheter 50 applies to the wall of the heart, to ensure proper contact between the contacts 62 or other devices provided on the elongate magnetic element 50 for conducting the medical procedure.

As shown in FIG. 4; the elongate magnet element 56 preferably has at least front and back faces 66 and 68, and the tethers 58 and 60 are preferably attached adjacent the back face 68. Thus, when a magnet gradient is applied, the elongate magnetic element 56 tends to orient with the front face 66 toward the gradient and thus toward the surface it is being pulled toward. This allows smaller contacts 62 to be positioned on the front face 66 of the elongate magnet element, rather than the larger ring contacts required on prior art catheters where the orientation could not be controlled. See the FIG. 5 enlarged side elevation view of the catheter 50 just before application to the wall of the patient's heart.

Figure 6:
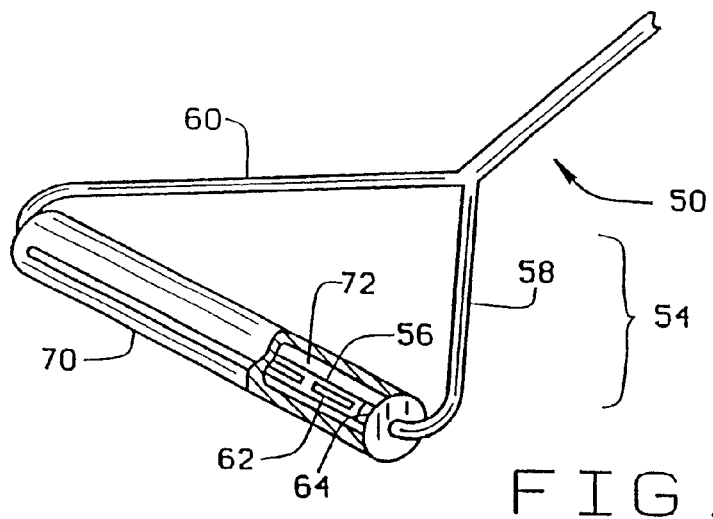
FIG. 6 is a perspective view of an alternate construction of the catheter of the second embodiment, with an envelope surrounding the elongate magnetic element.

As shown in FIG. 6, an elongate magnetic element 56 provided with ablation contacts 62 can be enclosed in a generally cylindrical envelope 70, which defines a volume 72 surrounding the elongate magnetic element 56. The volume 72 is filled with conductive fluid, such as a saline solution, and the envelope 70 has a narrow elongate porous window 74 permeable to the conductive fluid, to provide a conductive path from the contacts 62 through the conductive period to the exterior of envelope 70. The envelope 70 provides a protective buffer for the contacts 62 to prevent charring, and the window 74 provides a smooth, continuous narrow line of ablation.

As indicated above, the magnetic medical device, such as catheter 30 or 50, is navigated to the operating region, e.g., the chamber C of the heart. This can be conveniently done by putting the medical device in the distal end 82 of a sheath 80. The distal end 82 of the sheath 80 is navigated to the site, either mechanically, or magnetically (using the elongate magnetic elements). Once the distal end of the sheath 80 is at the surgical site, the magnetic medical device (either catheter 30 or 50) is deployed from the distal end of the sheath. This can be accomplished by pushing the proximal end of the magnetic medical device. Because the catheter is purposely made highly flexible, it can be difficult to push the medical device. A stylette can be inserted in the proximal end of the sheath to push the medical device from the sheath. A magnetic field can be temporarily aligned with the axis of the sheath 80 to help stiffen the elongate magnetic element, and facilitate its deployment from the sheath. A magnetic gradient can alternatively or additionally be applied to help pull the elongate magnetic element from the sheath. The front field gradient of a magnet could be used for this purpose.

Figure 7:
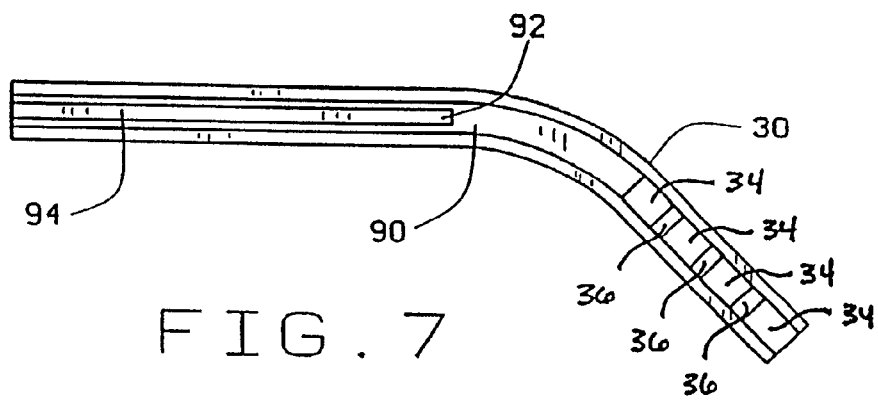
FIG. 7 is a longitudinal cross-sectional view of the catheter of the first embodiment with a stylette therein to stiffen the catheter for navigation to the surgical site.

As an alternative to navigating the magnetic medical device to the surgical site in a sheath 80, the device can-be navigated directly. The magnetic medical device is preferably highly flexible so that it is readily oriented and applied against structures at the surgical site. To facilitate its navigation to the surgical site, the catheter 30 (or 50) can be provided with a lumen 90, and as shown in FIG. 7 the distal end 92 of a stylette 94 can be inserted into the lumen to temporarily stiffen the catheter sufficiently for navigation. The catheter 30 can be navigated conventionally, or it can be navigated magnetically using the elongate magnetic element 36 on the distal end 34 of the catheter. Once at the surgical site, the stylette 94 can be removed to restore the flexibility of the catheter, and the aligning field and pulling gradient applied, as described above.

Figure 8:
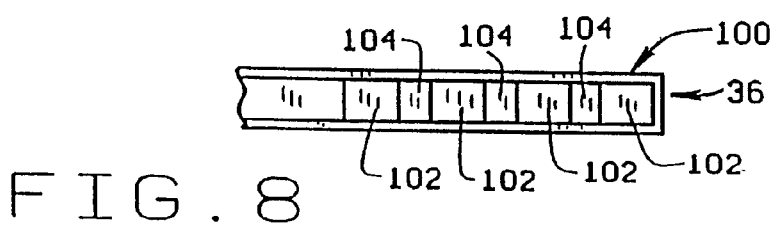
FIG. 8 is a longitudinal cross-sectional view of the elongate magnetic element.
Figure 9:
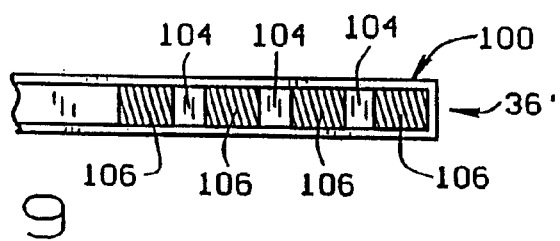
FIG. 9 is a longitudinal cross-sectional view of a first alternate construction of the elongate magnetic element.
Figure 10:
FIG. 10 is a longitudinal cross-sectional view of a second alternate construction of the elongate magnetic element.

An elongate magnetic element adapted for use with the method of this invention, and adapted to be incorporated into medical devices of this invention is indicated generally as 36 in FIG. 8. The elongate magnetic element 56 is similar in construction to elongate magnetic element 36. The elongate magnetic element 36 comprises a flexible hollow tube 100, having a plurality of magnetic bodies 102, separated by spaces 104. The spaces 104 allow the elongate magnet element 36 to flex to accommodate the surface of a body structure to which it is applied. The magnetic bodies 102 are preferably cylinders of a permanent magnetic material, such as neodymium iron boron, or cylinders of a permeable magnetic material. The contacts 38 are preferably aligned with the magnetic bodies 102 rather than the spaces 104, so that they are firmly pressed into the tissue upon the application of a gradient. An alternate construction of the elongate magnetic element is indicated generally as 36' in FIG. 9. In elongate magnetic element 36', the magnetic bodies 102 are coils 106 of a magnetically responsive material, such as a permeable magnetic material (such as soft iron or hyperco) or a permanent magnetic material. A second alternate construction of the elongate magnetic element is indicated generally as 36" in FIG. 10. In elongate magnetic element 36", the magnetic bodies 102 comprise a single elongate coil 108 of a magnetically responsive material, such as a permeable magnetic material or a permanent magnetic material.

In a preferred construction of the catheter 30, the catheter comprises a continuous tube, with elongate magnet element being disposed in the distal portion of the tube. The proximal portion of the continuous can be made stiffer to improve the ability to advance the catheter by pushing, while leaving the distal end flexible to allow the elongate magnetic element to respond to applied magnetic fields and gradients. The continuous tube forms a tether for restraining the elongate magnetic element formed in the distal section against the pull of the magnetic gradient. The tube has a lumen for electrical leadlines, or cryogen pathway, or a fluid pathway for whatever medical device(s) is provided on the elongate magnetic element on the distal end.

In a preferred construction of the catheter 50, one or both of the tethers 58 and 60 excluding the elongate magnetic element 56 are hollow tubes, communicating with a lumen through the catheter. The tethers thus provide a continuous path through the catheter 50 to the elongate magnetic element for electric leadlines, a cryogen pathway, or a fluid pathway for whatever medical device(s) is provided on the elongate magnetic element. The tethers 58 and 60 are preferably highly flexible to allow the elongate magnetic element to freely respond to an applied magnetic field or gradient.

Figure 11A:
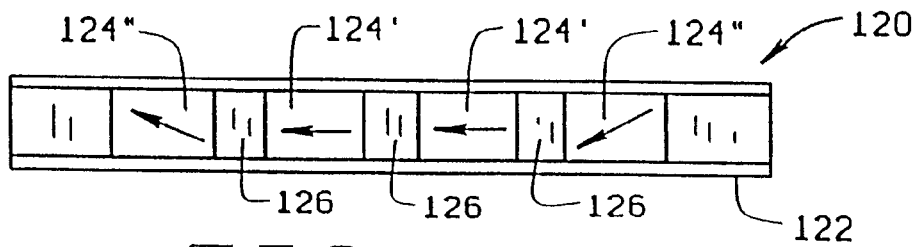
FIG. 11A is a longitudinal cross-sectional view of an alternate embodiment of the elongate magnetic element, predisposed to curve under the application of a magnetic field to a concave surface.
Figure 11B:
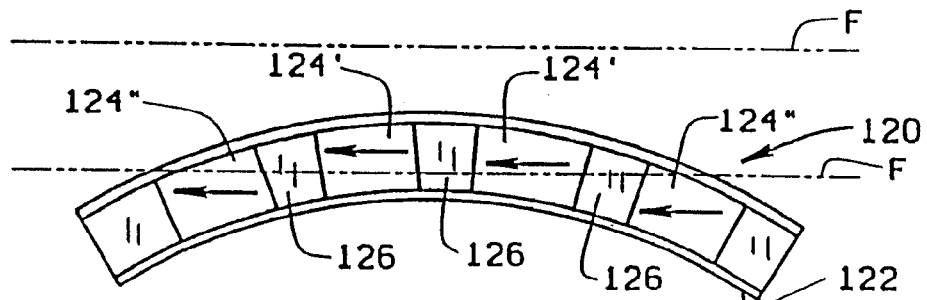
FIG. 11B is a longitudinal cross-sectional view of the alternate embodiment of the elongate magnetic element shown in FIG. 10A, as it curves under the application of a magnetic field.

Because of the tendency of the elongate magnetic element to rigidly align with the applied magnetic field lines, which are typically straight when using the side field of a magnet, the elongate magnetic element may not conform to the curved surface of a body structure, such as the walls of the chamber of a heart, although the heart will conform somewhat to the catheter. An alternative embodiment of the elongate magnetic element indicated as 120 in FIGS. 11A and 11B, is adapted to conform to the curved surface of a body structure. Elongate magnetic element 120 is similar in construction to elongate magnetic element 36, comprising a flexible hollow tube 122 having a plurality of magnetic bodies 124, separated by spaces 126. The spaces 126 allow the elongate magnet element to flex to accommodate the surface of a body structure to which it is applied. The magnetic bodies 124 are preferably cylinders of a permanent magnetic material, such neodymium iron boron, with their polarities arranged to facilitate the application of the elongate magnetic element to a curved surface. Thus, as shown in FIG. 11A, the polarities of the magnetic bodies 124' in the center are generally parallel to the axis of the tube 122, while the polarities of the magnet bodies 124" at the ends are at an oblique angle to the axis of the tube 122. This arrangement causes the elongate magnetic element 120 to bend when a magnetic field with relative straight field lines is applied to the elongate magnetic element, as shown in FIG. 11B.

Figure 12A:
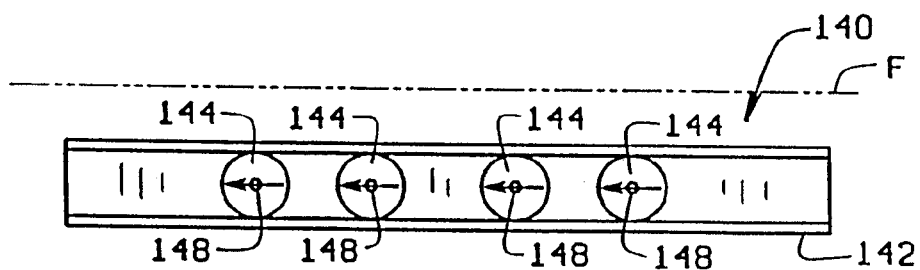
FIG. 12A is a longitudinal cross-sectional view of an alternate embodiment of the elongate magnetic element, that can curve to conform to a body structure, even under the application of a straight magnetic field.
Figure 12B:
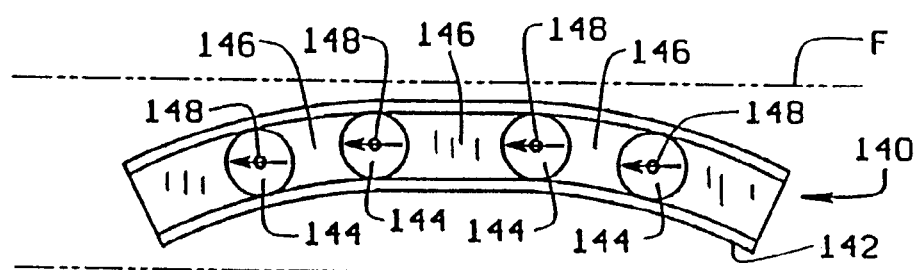
FIG. 12B is a longitudinal cross-sectional view of the alternate embodiment of the elongate magnetic element shown in FIG. 11A, as it conforms to a curved surface even under the application of a straight magnetic field.

An alternative way of increasing the conformability of the elongate magnetic element to a curved surface is to allow the magnetic bodies to pivot to remain aligned with the field, as the elongate magnetic member bends to conform to the surface to which it is applied. However, the magnetic bodies must be sufficiently spaced that they can pivot independently in the applied magnetic field. Thus, an alternative construction of an elongate magnetic device, indicated generally as 140 in FIGS. 12A and 12B, is adapted to conform to the curved surface of a body structure. Elongate magnetic element 140 comprises a flexible hollow tube 142, having a plurality of magnetic bodies 144, separated by spaces 146. The spaces 146 allow the elongate magnet element to flex to accommodate the surface of a body structure to which it is applied. The magnetic bodies 144 are preferably spheres of a permanent magnetic material, such neodymium iron boron, mounted to pivot in the tube 142 about an axis perpendicular to the polarity. Thus as shown in FIG. 10A, the polarities of the magnetic bodies 144 align and can orient the elongate magnetic element 140, but as shown in FIG. 10B, when the elongate magnetic element 140 is applied to the surface of a body structure, the magnet bodies 144 at the ends can pivot so that they remain aligned with the applied magnetic field. The spheres are pivotally mounted, for example on pins 148, which allow the spheres 144 to pivot about parallel axes, but which secure the spheres relative to tube 142 so that the tube can rotate with rotation of the field.

Operation

A magnetic medical device, such as catheter 30 or 50, is navigated to the surgical site within an operating region, for example a chamber of the heart. The catheter 30 or 50 can have contacts thereon such as electrodes for cardiac mapping or cardiac pacing, or contacts for cardiac tissue RF-ablation, ultrasonic ablation, or cryogenic ablation. Alternatively the catheter 30 or 50 could have injectors, or simply openings for delivering substances, such as saline for cooling the RF-ablation contacts, or therapeutic agents. Of course other diagnostic or therapeutic elements and devices could be provided on the catheters 30 and 50.

The catheter 30 or 50 can be navigated to the chamber of the heart in the distal end of a sheath 80. The sheath can be mechanically navigated, as is known in the art. It is also possible to magnetically navigate the distal end of the sheath, taking advantage of the elongate magnetic element 36 of the catheter 30 (or the elongate magnetic element 56 of the catheter 50). Once the distal end of the sheath 80 is at the surgical site, the catheter 30 or 50 is deployed by pushing the proximal end to eject it from the distal end of the sheath. A magnetic field can be applied to stiffen the elongate magnetic element 36 of catheter 30 (or the elongate magnetic element 56 of catheter 40), to facilitate its deployment from the end of the sheath.

Alternatively the catheters, and particularly catheter 30 can be navigated to the surgical site directly. This can be a simple mechanical navigation, with the assistance of a stiffening stylette 94, or it can be magnetically assisted navigation taking advantage of the elongate magnetic element that is part of the catheter. The front field of a magnet can be used to align the elongate magnetic element and apply a pulling gradient in the same direction as the magnetic field (as opposed to the side field utilized in the present invention which is generally oblique to the field direction). A standard curved catheter can be used to facilitate navigating the device to the desired chamber, where it can be deployed.

Once it is deployed, a magnetic field and gradient is applied to the magnetic element 36 of catheter 30 (or 56 of catheter 50). The field tends to align the elongate magnetic element with the local field lines while the gradient tends to pull the elongate magnetic element toward the wall of the heart chamber. The movement of the elongate magnetic element 36 is restrained by the proximal portion of the catheter 30. The movement of the elongate magnetic element 56 is restrained by the proximal portion of the catheter 50 and the tethers 58 and 60. The magnetic field direction is manipulated (typically by moving the magnet or magnets applying the field and gradient) to orient the elongate magnetic element in the desired orientation. Once in the desired orientation, the elongate magnetic element can be applied to the surface of the chamber wall by slacking the proximal end of the catheter 30 or 50. The elongate magnetic element is pulled by the magnetic gradient into contact with the wall of the chamber. The position of the elongate magnetic element can be tracked by the markers 40 (or 64 on catheter 50). Once the position of the elongate magnetic element can be located relative to the magnet(s) applying the magnetic field and gradient, the force applied by the elongate magnetic element can be determined, and controlled by varying the position of the magnet. Thus, the force with which the contacts on the elongate magnetic element are applied to the tissue can be ascertained and controlled.

When it is desired to reposition the elongate magnetic element, the magnet(s) can simply be manipulated to reorient the elongate magnetic element while the elongate magnetic element remains in contact with the surface of the chamber wall. Preferably however, the elongate magnetic is pulled out of contact with the chamber wall by tensioning the proximal end of the catheter 30 or 50, and the elongate magnetic element is re-oriented out of contact with the chamber wall, and reapplied by slacking the tension on the proximal end of the catheter 30 or 50.

When the procedure is completed, the catheter 30 or 50 is removed from the surgical site, for example retracting it into the sheath 50 and withdrawing the sheath, or by withdrawing the catheter directly.

Figure 13:
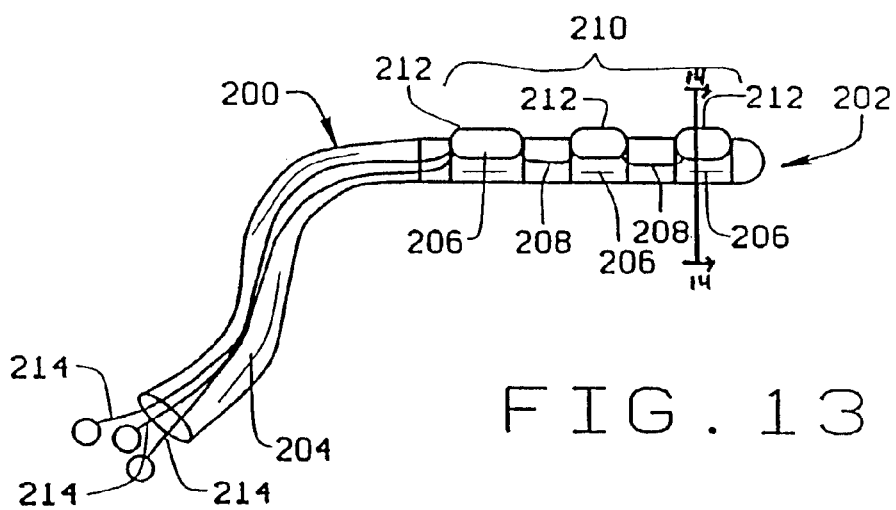
FIG. 13 is a longitudinal cross-sectional view of an electrophysiology catheter constructed according to the principles of this invention.
Figure 14:
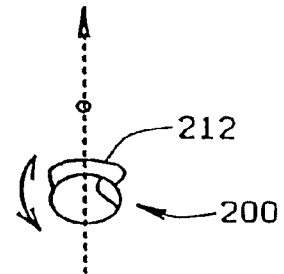
FIG. 14 is a transverse cross-sectional view of the electrophysiology catheter, taken along the plane of line 14—14 in FIG. 13.
Figure 15:
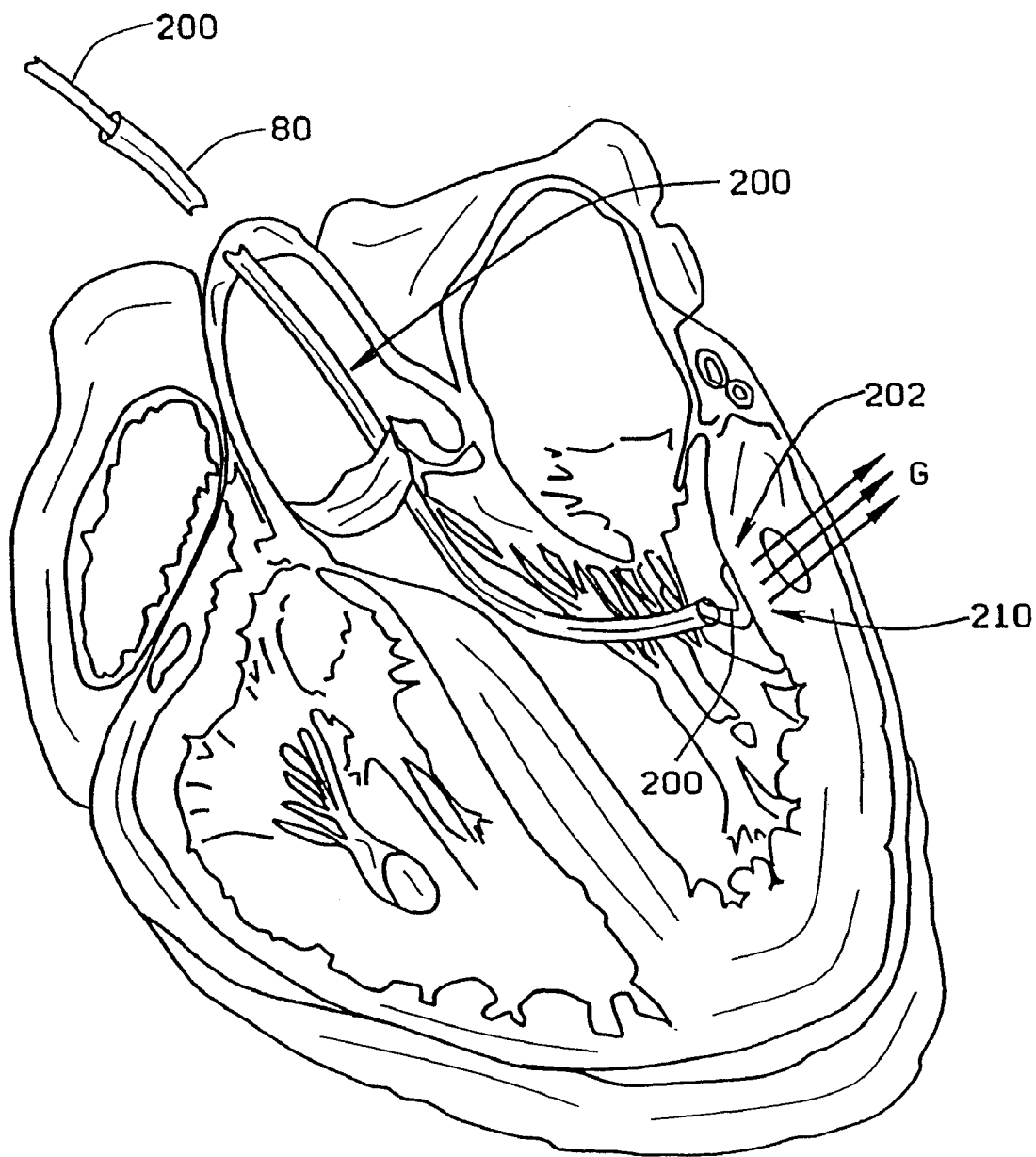
FIG. 15 is a perspective view of a heart showing the electrophysiology catheter in a chamber for application to the wall of the chamber.

An electrophysiology catheter constructed according to the principles of this invention is indicated generally as 200 in FIGS. 13–15. Catheter 200 has a proximal. end, a distal end 202, and a lumen 204 therebetween. There are a plurality of magnetic bodies 206 separated by spaces 208, forming an elongate magnetic element 210 adjacent the distal end 202. There are a plurality of electrodes 212 spaced along the elongate magnetic element 210. A lead 214 extends through the lumen 204 to the electrodes 212. Markers 2165 are incorporated into the catheter 200 to facilitate localizing the catheter in the body.

The distal end 202 of the catheter 200 is navigated through the vasculature, and into the chamber of the heart. Once the distal end 202 of the catheter is in the chamber of the heart, a magnetic field and an oblique magnetic gradient are applied to the distal end. As shown in FIG. 14, the field aligns the elongate magnetic element 210 with the applied magnetic field. The magnetic gradient G, in a direction oblique to the magnetic field direction, pulls the elongate magnetic element toward the wall of the chamber.

The electrodes 212 are brought into contact with the wall of the chamber. RF energy is applied to the electrodes 212 via leads 214 (either simultaneously or serially). The RF energy ablates the tissue adjacent the electrodes forming a linear lesion useful in treating various tachyarrhythmias. The elongate magnetic element 210 can be pulled from the chamber wall by tensioning the proximal portion of the catheter 200. The elongate magnetic element 210 can be re-oriented by changing the magnetic field by repositioning andor reorienting the source of the field. The tension on the proximal portion of the catheter is slackened and the magnetic gradient pulls the elongate magnetic element back into contact with the chamber wall. RF energy can be applied to create another linear lesion by ablation. The process continues until the desired linear lesions have been formed, the intent being to create a continuous linear lesion build up from these segments.

Figure 16:
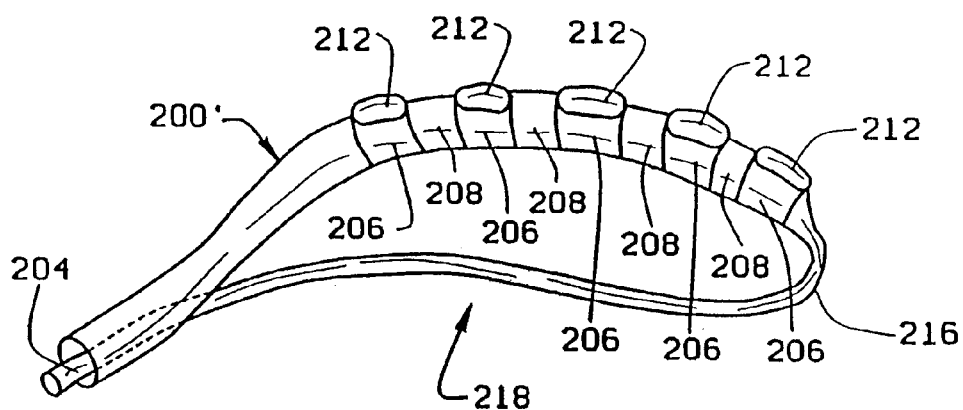
FIG. 16 is a perspective view of an alternate condiment of electrophysiology catheter.

An alternate construction of the catheter 200 is indicated generally as 200' in FIG. 16. Catheter 200' is similar in construction to catheter 200, and corresponding reference numerals indicate corresponding parts. However, unlike catheter 200, catheter 200' has a tether 216 extending from its distal end. The tether 216 passes through an opening in the wall of catheter, and then through the lumen to the proximal end, where the tether can be manipulated to change the shape of the elongate magnetic element 210 by expanding and contracting the loop 218.

What is claimed is:

1. A medical device adapted to align with an externally applied magnetic field, and be pulled against the surface of an internal body structure by an externally applied magnetic gradient, the medical device comprising:

an elongate magnetic element having first and second ends and comprising a plurality of magnetically responsive bodies spaced along the length of the element, and a tether extending from each end of the elongate magnetic element for restraining the elongate magnetic element against the force of the applied magnetic gradient; the elongate magnetic element has at least first and second faces, and wherein the tethers are secured adjacent the first face, so that under the applied gradient, the second face faces the surface of the body structure.

2. The medical device according to claim 1 wherein there are medical elements on the second face of the elongate magnetic element, which contact the surface of the body structure.

3. The medical device according to claim 1 further comprising at least one contact on the second face of the elongate magnetic element for ablating tissue to which it is applied.

4. The medical device according to claim 3 wherein the at least one contact is an RF electrode for ablating tissue with RF energy.

5. The medical device according to claim 3 wherein the at least one contact is a cryogenic contact for ablating tissue by freezing.

6. The medical device according to claim 3 wherein the at least one contact is an ultrasonic transducer for ablating tissue by ultrasound.

7. The medical device according to claim 1 further comprising at least one electrode on the elongate magnetic element for electrically mapping the surface to which it is applied.

8. The medical device according to claim 1 further comprising at least one electrode on the elongate magnetic element for applying a pacing signal to the surface to which it is applied.

9. The medical device according to claim 1 further comprising markers on the device for locating the device inside the body.

10. The medical device according to claim 9 wherein the markers are locatable with at least one of fluoroscopy; ultrasound, or electromagnetic localization techniques.

11. The medical device according to claim 1 wherein the elongate magnetic element comprises openings therein for ejecting a substance from the medical device.

* * * * *